(12) United States Patent
Fourcault et al.

(10) Patent No.: US 7,846,163 B2
(45) Date of Patent: Dec. 7, 2010

(54) DEVICE DESTINED TO BE COUPLED TO AT LEAST ONE SUPPORT, AND IN PARTICULAR A SURGICAL IMPLANT DESTINED TO BE COUPLED TO A BONE

(75) Inventors: Eric Stéphane Fourcault, Lyons (FR); Theo Jan Maria Knevels, Grimbergen (BE); Jean-Christophe Alain Giet, Lyons (FR); Bertrand Xavier François Gauneau, Lyons (FR)

(73) Assignee: Newdeal, Lyons (FR)

( * ) Notice: Subject to any disclaimer, the term of this patent is extended or adjusted under 35 U.S.C. 154(b) by 1563 days.

(21) Appl. No.: 10/869,126

(22) Filed: Jun. 16, 2004

(65) Prior Publication Data

US 2005/0015131 A1    Jan. 20, 2005

(30) Foreign Application Priority Data

Jun. 16, 2003   (FR) .................................. 03 07237

(51) Int. Cl.
  *A61B 17/58* (2006.01)
  *A61B 17/80* (2006.01)
(52) U.S. Cl. .................. 606/68; 606/246; 606/280; 606/288; 606/290
(58) Field of Classification Search .................... 606/61, 606/69, 288, 290
  See application file for complete search history.

(56) References Cited

U.S. PATENT DOCUMENTS

| 5,954,722 A | * | 9/1999 | Bono ............................ 606/61 |
| 6,235,033 B1 | | 5/2001 | Brace et al. .................... 606/69 |
| 7,220,263 B2 | * | 5/2007 | Cordaro ........................ 606/69 |
| 2002/0045898 A1 | * | 4/2002 | Freid et al. ..................... 606/61 |
| 2002/0045901 A1 | * | 4/2002 | Wagner et al. ................. 606/69 |
| 2003/0023240 A1 | * | 1/2003 | Amrein et al. ................. 606/61 |
| 2003/0105462 A1 | * | 6/2003 | Haider .......................... 606/69 |
| 2004/0127900 A1 | * | 7/2004 | Konieczynski et al. ........ 606/69 |

FOREIGN PATENT DOCUMENTS

| EP | 0 345 133 A | 12/1989 |
| FR | 2 790 198 A | 9/2000 |
| WO | WO 99 59492 A | 11/1999 |

* cited by examiner

*Primary Examiner*—Thomas C Barrett
*Assistant Examiner*—Sameh Boles
(74) *Attorney, Agent, or Firm*—Thomas, Kayden, Horstemeyer & Risley, LLP

(57) ABSTRACT

Disclosed herein is a device destined to be coupled to at least one support, and in particular a surgical implant destined to be coupled to a bone. The invention relates generally to a device (1) including a fixing element (3) including a head (3A) and a pin (3B) destined to be anchored in a support. The device further includes an assembly part (4) including a through hole (5), and a ring (6) housed in a manner that can be oriented within the through hole (5). The ring (6) has a passage (6A) shaped so as to allow passage of the pin (3B) and to stop the head (3A). The ring (6) is expandable according to its axial direction between a configuration wherein the ring (6) can be oriented and a configuration wherein the ring (6) is blocked.

17 Claims, 2 Drawing Sheets

DEVICE DESTINED TO BE COUPLED TO AT LEAST ONE SUPPORT, AND IN PARTICULAR A SURGICAL IMPLANT DESTINED TO BE COUPLED TO A BONE

CROSS-REFERENCE TO RELATED APPLICATION

This application claims priority to copending French application entitled, "Device Destined to be Coupled to at Least One Support, and in Particular a Surgical Implant Destined to be Coupled to a Bone," having application no FR-03 07237, filed Jun. 16, 2003, which is entirely incorporated herein by reference.

TECHNICAL FIELD

This invention relates to the technical field of devices destined to be solidly fastened to a support, in view for example to consolidate or repair said support, or to equip this support with an additional functional and/or decorative item constituted by the device.

This invention relates to a device destined to be coupled to at least one support, said device comprising:
- a fixing element including a head and a pin destined to be anchored in the support,
- an assembly part comprising at least one through hole,
- a ring housed in a manner that can be oriented within said through hole, said ring having a passage shaped so as on the one hand to allow passage of the pin and on the other hand to realize a means of stoppage for the head.

This invention also relates to, independently from the rest of the device in accordance with the invention, an assembly part used in the framework of this device.

This invention also relates to, independently from the rest of the device, a ring destined to be used within the framework of the device in accordance with the invention.

The invention furthermore relates to a surgical implant destined to be coupled to a bone support, said implant having an upper side and an opposite lower side, and comprising at least one through hole arranged between said lower and upper sides.

Finally, the invention relates to a ring destined to receive an osteosynthesis screw.

The invention is more particularly directed to a surgical device, of the implant type, destined to be assembled to a bone or to bone fragments, but it may also apply to any other field, such as construction and do-it-yourself.

BACKGROUND

In what follows, in a purely illustrative and non-limiting manner, reference will be made generally to the medical field.

Document discloses EP-345 133 a surgical implant destined to be assembled to a bone using a screw. The surgical implant described in this document includes a passage through which passes the screw, and a countersink with external threading of which the diameter is greater than that of the head of the screw, so as to define a root constituting a support surface for said head.

A check screw is received and screwed into this countersink, by exercising on the head of the fixing element an axial compression effort which applies it against the root of the countersink.

Such a fastening principle, which consists in solidly fastening and blocking the head of the screw relative to the implant by the check screw, makes it possible to benefit from a sealing effect realized by the anchoring of the screw in the bone on one hand, and the fastening of the implant on the screw on the other hand.

Thus, contrary to more traditional arrangements, the positive connection of the bone and implant described in document EP-345 133 does not depend on a compression force that applies them together, nor consequently on the forces of friction at the level of the implant/bone interface.

Consequently, even when the bone matter is degraded at the level of the implant/bone interface, the implant described in document EP-345 133 remains mounted in a stable manner, since the bone/implant contact is not imperative in order to ensure that the mounting holds.

This character of stability favors bone reconstruction, and makes it possible to minimize surgical and postoperative difficulties, which contributes to restoration of the patient in the best conditions.

The device described in document EP-345 133 has however the inconvenience of not being able to freely fix the orientation of the screw relative to the implant.

The device described in this document only authorizes in fact a single angular positioning of the screw relative to the implant.

However, it is particularly interesting to have a system that can be oriented at will, in particular in traumatology, for example to approach an isolated bone fragment.

Furthermore, in the particular case where the implant is an osteosynthesis plate, it is shown to be generally indicated to vary the angles of the security screw relative to the plate, so as to benefit from anchoring according to axes that cross amongst themselves, which limits the effect of pulling of the plate when the latter is subjected to mechanical efforts of the type normal traction, bending or other.

In this case, it is shown to be interesting to be able to select, at the time of placing, the screw angulations, so as to adapt them to the particular anatomical constraints of the patient operated on.

Document FR-2 790 198 discloses an implant system making it possible to freely determine the screw angulation in relation to the implant.

The system described in this document includes an implant equipped with an orifice within which is positioned a radially expanding ring wherein the security screw is screwed.

Said screw has a radial enlargement near its head, such that at the end of screwing, this enlargement causes the ring to expand radially and the blocking of the latter in position against the walls of the orifice.

Such a system does not make it possible however to benefit from a sealing effect equivalent to that provided by the arrangement described in document EP-345 133 previously mentioned.

Moreover, the system described in document FR-2 790 198 requires the use of an instrument to tighten the screw as well as an instrument for blocking the ring during the tightening of the screw. Consequently, the two hands of the surgeon are solicited simultaneously, which complicates the operating task.

Furthermore, the arrangement proposed by document FR-2 790 198 exposes the ring to excessive expulsions from the orifice, since the ring is retained within the orifice only and exclusively par the forces of friction generated by the radial pressure exerted by the radial enlargement of the screw.

Finally, in the system described by document FR-2 790 198, blocking the screw in position relative to the implant occurs at the same time as the tightening of the screw in the bone, according to a single tightening gesture. Other than the fact that such a confusion of tasks does not make it possible to realize accurately, in terms notably of intensity of effort, the tightening in the bone as well as the blocking in angular position, certain mountings are revealed in practice to be extremely delicate to realize. This is the case for example with piled mountings, where the implant, after mounting, is located at a considerable distance from the bone.

SUMMARY

The object of the invention aims consequently to provide a solution to the different inconveniences listed above and to propose a new device, notably a surgical implant, equipped with a fixing element and destined to be coupled to at least one support, notably bone, of which the design makes it possible to realize a particularly stable assembly, while authorizing any angular orientation of the fixing element relative to the support.

Another object of the invention aims to propose a new device, notably a surgical implant, equipped with a fixing element and destined to be coupled to at least one support, notably bone, of which the design facilitates the search for a precise geometric orientation of the fixing element.

Another object of the invention aims to propose a new device, notably a surgical implant, equipped with a fixing element and destined to be coupled to at least one support, notably bone, of which the design authorizes a blocking of the head of the fixing element relative to the device.

Another object of the invention aims to propose a new device, notably a surgical implant, equipped with a fixing element and destined to be coupled to at least one support, notably bone, of which the design allows dissociation between the action of anchoring the fixing element in the support and the action of blocking the fixing element in a determined angular position.

Another object of the invention aims to propose a new device, notably a surgical implant, equipped with a fixing element and destined to be coupled to at least one support, notably bone, which has a removable character.

Another object of the invention aims to propose a new device, notably a surgical implant, equipped with a fixing element and destined to be coupled to at least one support, notably bone, whose implementation is particularly reliable.

Another object of the invention aims to propose a new device, notably a surgical implant, equipped with a fixing element and destined to be coupled to at least one support, notably bone, of which the manufacture is particularly simple and rapid and makes it possible to avoid any excessive disassembly of the items comprising the device.

The objects attributed to the invention are reached using a device destined to be coupled to at least one support, said device including:
  a fixing element including a head and a pin destined to be anchored in the support,
  an assembly part including at least one through hole,
  a ring housed in a manner that can be oriented within said through hole, said ring being equipped with a passage shaped on one hand to allow passage of the pin, and on the other hand to realize a means of stoppage for the head,
  wherein the ring is expandable according to substantially its axial direction between an initial configuration wherein the ring can be oriented relative to the hole and an expanded configuration wherein the ring is blocked relative to the hole.

The objects attributed to the invention are also reached using an assembly part for the device in accordance with the invention.

The objects attributed to the invention are also reached using a ring of the device in accordance with the invention.

The objects attributed to the invention are also reached using a surgical implant destined to be coupled to a bone support, said implant having an upper side and an opposite lower side and including at least one through hole arranged between said upper and lower sides, characterized in that the transversal section of said hole at the level of the upper and/or lower side has a general substantially circular shape, with two additional diametrically opposed undercuts.

The objects attributed to the invention are finally also reached using a ring destined to receive an osteosynthesis screw characterized in that said ring includes substantially rigid first and second items said items being superimposed and connected by a flexible part.

BRIEF DESCRIPTION OF THE DRAWINGS

Other advantages and objects of the invention shall appear in more detail as the disclosure that follows is read, and using the annexed drawings provided in a purely illustrative and non-limiting manner, wherein.

DETAILED DESCRIPTION OF THE PREFERRED EMBODIMENTS

Figure 1:
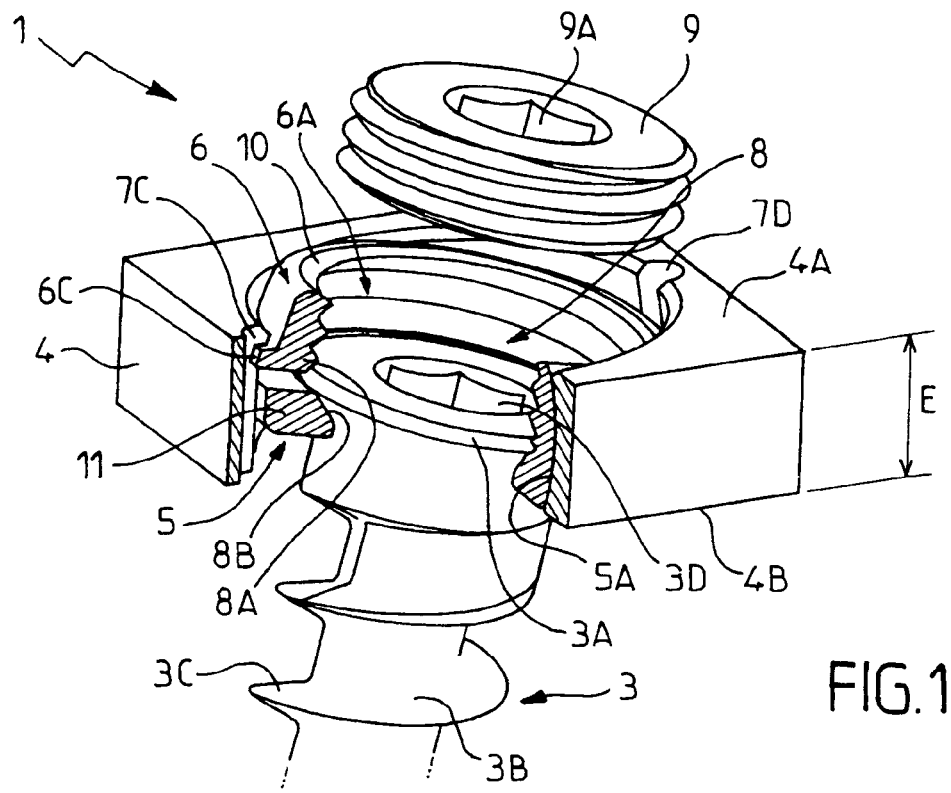
FIG. 1 shows, according to a cutaway view in perspective, an example of realization of a device in accordance with the invention.
Figure 2:
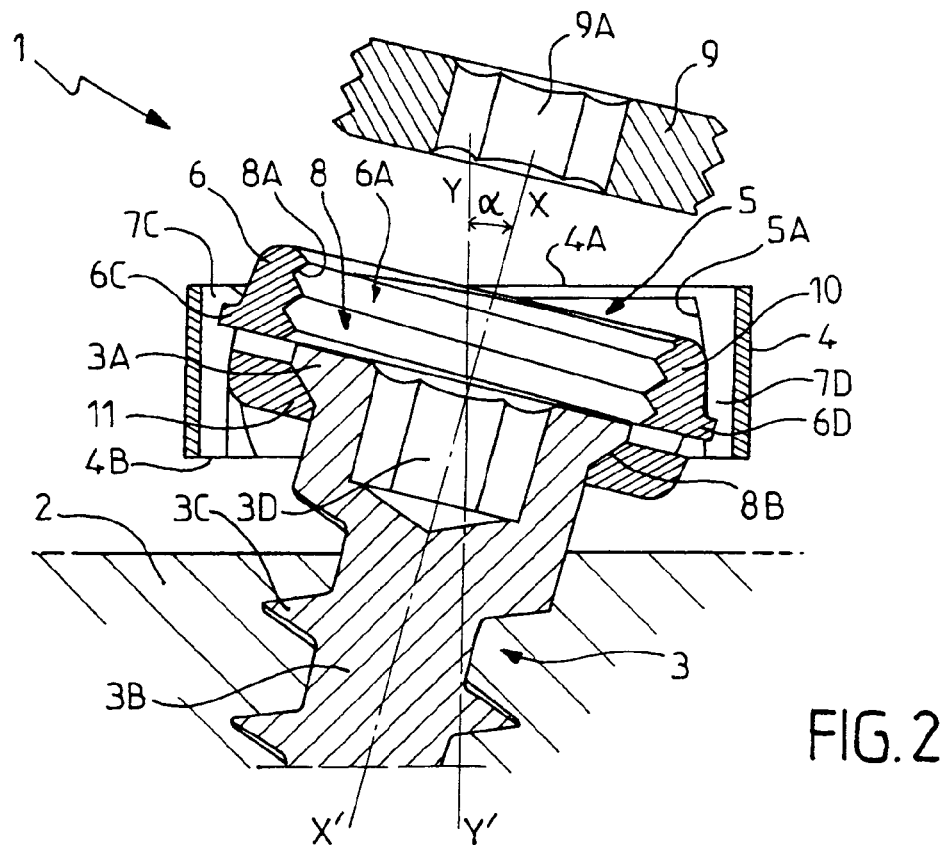
FIG. 2 shows, according to a cutaway side view, the device shown in FIG. 1.
Figure 3:
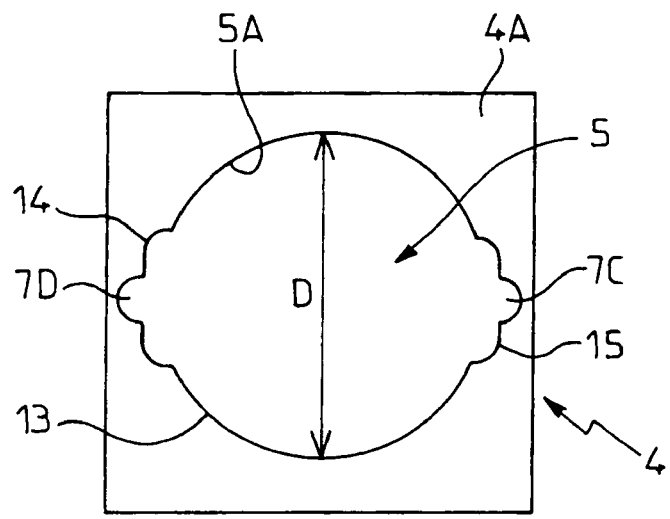
FIG. 3 shows, according to an overhead view, an assembly part that is part of the device in accordance with the invention shown in FIGS. 1 and 2.

FIGS. 1 and 2 show a device 1 destined to be coupled to at least one support 2, in view to form an assembly with said support 2.

In what follows, reference shall be made to device 1 of surgical nature, support 2 being made of bone matter. Nevertheless, in the sense of the invention, device 1 in accordance with the invention can be of any nature, the same as support 2 to which it is destined to be fastened.

Device 1 in accordance with the invention includes a fixing element 3 comprising a head 3A as well as a pin 3B destined to be anchored in support 2.

As shown in FIGS. 1 and 2, the fixing element 3 is more preferably a screw. In this case, the pin 3B is equipped more preferably with external threading 3C. Head 3A includes, more preferably, a tapered skirt (better seen in FIG. 2) followed by a smooth area with a general substantially cylindrical shape. Head 3A is more preferably equipped with rivet seam 3D, of the six sided river seam type, destined to receive a corresponding spanner wrench with the view to carry out the tightening of pin 3B into support 2.

It is however possible to consider, without leaving the framework of the invention, that fixing element 3 be constituted by any other alternative means, well known by those skilled in the art, and for example by a nail.

Device 1 in accordance with the invention includes also an assembly part 4 destined to be solidly attached to support 2.

In a more preferable application of the invention, assembly part 4 is a surgical ancillary or implant, destined to be associated to support 2 of a bone nature. More preferably, assembly part 4 is a surgical osteosynthesis plate destined for example for reducing a bone fracture.

In this case, plate 4 is a joint between the different fragments of the fractured bone, each fragment being joined to plate 4 through the intermediary of at least one fixing element 3.

It is also possible to consider, by way of example, that assembly part 4 be comprised of a grooved implant. In what follows, reference will be made more particularly to an assembly part 5 composed of a surgical implant, since the invention can find application in many other sectors, such as construction and do-it-yourself for example.

In accordance with the invention, assembly part 4 includes at least one through hole 5. Said through hole 5 is an orifice from one side to the other of assembly part 4, across all of its thickness E, between its upper side 4A and its opposite lower side 4B. Said lower side 4B is destined to be positioned facing support 2.

Device 1 includes also a ring 6, i.e. an annular element, housed in a manner that can be oriented within through hole 5.

Through hole 5 constitutes as such a cavity that forms a housing that receives ring 6, more preferably in a captive manner.

The ring 6 can be oriented in a variable manner. We designate here that the axial direction X-X' attached to ring 6 can be determined freely, for example by a surgeon, and notably be different for axial direction Y-Y' attached to the assembly part 4. Axial directions X-X' and Y-Y' correspond respectively substantially to the axis of symmetry of ring 6 and through hole 5. Thus, within the limits of a predetermined range, angle α present between the respective axial directions X-X', Y-Y' of ring 6 and of assembly part 4 shall be able to be selected and fastened at will by the user.

Ring 6 is equipped moreover with a passage 6A which completely passes through its thickness $\underline{e}$. Said passage 6A is shaped on one hand to allow the passage of pin 3B of fixing element 3, and on the other hand to realize a means of stoppage for head 3A of fixing element 3. Thanks to this arrangement, it is possible to completely insert the fixing element 3 into ring 6 until head 3A is stopped by a sizing of passage 6A forming a means of stoppage. It is therefore understood that more preferably, the overall diameter of pin 3B of fixing element 3 is less than the minimum diameter of passage 6A.

In accordance with an important characteristic of the invention, ring 6 is expandable according to substantially its axial direction X-X' between on one hand its initial configuration, wherein ring 6 maintains its capacity to be freely oriented to the hole, and on the other hand an expanded configuration, wherein ring 6 is blocked in a determined angular position relative to through hole 5. In other terms, ring 6 has the capacity to bend axially, i.e. to have its thickness $\underline{e}$increase to bring it from an initial configuration wherein said ring 6 can be oriented relative to hole 5 to an expanded configuration wherein ring 6 is wedged, i.e. mechanically countersunk in through hole 5.

Thus, the general principle of the invention relies primarily on the implementation of a ring 6 which has the capacity to geometrically change shape according to the axial direction X-X' that is attached to it, this axial expansion comes to modify the overall space that ring 6 occupies, such that the latter comes up against wall 5A of the cavity formed by through hole 5, which has for effect to substantially suppress all freedom of movement between ring 6 and assembly part 4.

The principle of the invention thus relies on a dimensional variation in the axial direction X-X' of ring 6 and not, as in prior art, on the radial pressure exerted by a lug against the wall of a through hole.

Favorably, through hole 5 and ring 6 are shaped to realize together a spherical kinematic joint (also called a ball-and-socket joint) between assembly part 4 and ring 6 when the latter is in its initial configuration, i.e. not expanded.

More preferably, this spherical joint can be obtained in a traditional manner by shaping through hole 5 such that its internal wall 5A has a shape that is substantially similar to a spherical band (i.e. a spherical surface amputated of its two polar caps), the ring 6 having a complementary exterior lateral contour 6B that is adjusted to that of internal wall 5A of the through hole 5.

Thus, when axial directions X-X' and Y-Y' attached respectively to ring 6 and to through hole 5 are aligned, the contour 6B of 6 substantially hugs internal wall 5A. Even more preferably, through hole 5 and ring 6 are shaped to realize a spherical kinematic joint catch between ring 6 and assembly part 4 when said ring 6 is in its initial configuration, said spherical joint catch substantially prohibiting the rotation of ring 6 around its axial direction X-X'.

In other terms, the spherical joint catch allows the same relative movements of ring 6 and hole 5 as the spherical joint mentioned previously, except for the fact that this time, the rotation of ring 6 on itself around its axis of symmetry X-X' is substantially prevented.

Figure 4:
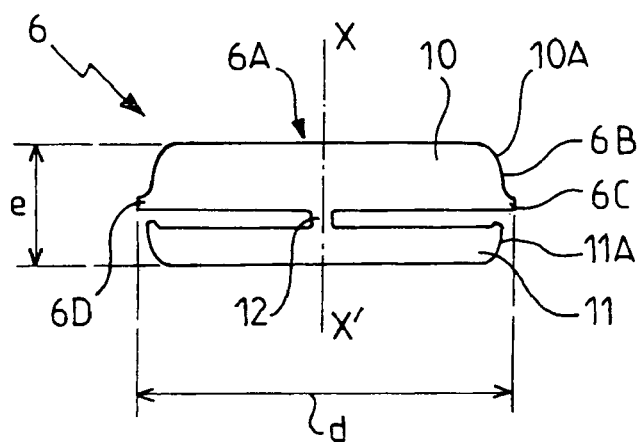
FIG. 4 shows, according to a side view, a ring that is part of the device in accordance with the invention shown in FIGS. 1 and 2.

More preferably, this spherical joint catch is realized in the same manner as the spherical joint previously described, with the difference that ring 6 includes at least one radial fin 6C, and more preferably two radial fins 6C, 6D opposed diametrically, such as is shown in FIG. 4. Said radial fins 6C, 6D thus form a bump relative to the lateral external contour 6B of ring 6. Each radial fin 6C, 6D is destined to cooperate with a corresponding groove 7C, 7D of complementary shape arranged longitudinally in a rectilinear manner, on all or a portion of lateral wall 5A of through hole 5, more preferably parallel to the axial direction Y-Y' attached to hole 5 and assembly part 4.

The cooperation of fins 6C, 6D with the corresponding grooves 7C, 7D according to substantially a sliding kinematic joint thus allowing to prohibit only the rotation of ring 6 around its axial direction X-X' that is attached to it.

It is however completely possible to consider, without leaving the framework of the invention, to allow for any other type of kinematic joint between ring 6 and assembly part 4 making an angulation possible of said ring 6 relative to part 4. For example, a free kinematic joint can be considered between ring 6 and through hole 5, i.e. that ring 6 is simply contained in through hole 5, the latter not providing any particular guiding function. By way of example, it can thus be considered that through hole 5 has a substantially rectangular section, while ring has an external contour 6B that is partially or totally polyhedral, which is therefore not complementary with that of internal wall 5A of hole 5.

Favorably, passage 6A arranged in ring 6 includes an internal threaded countersink 8 defining, in a traditional manner, on one hand a bore with internal threading 8A and on the other hand a root 8B, this root 8B forms a support surface and means of stoppage for head 3A of the fixing element 3.

Thus, head 3A comes to rest at the limit on the shoulder forming root 8B. The diameter of bore with internal threading 8A is thus more preferably greater than the overall diameter of all of fixing element 3, while the diameter of passage 6A at the level of the restriction of section forming root 8B is greater than that of pin 3B, but less than that of head 3A.

Device 1 in accordance with the invention includes also a check screw 9 destined to be received and screwed into countersink 8 against head 3A of fixing element 3, such that said head 3A is interposed between root 8B and check screw 9.

Check screw 9 is more preferably presented in the form of a cylindrical lug with external threading equipped with a driving recess 9A, which is destined to receive a tightening tool.

More preferably, the driving recess 3D of fixing element 3 and driving recess 9A of check screw 9 are of identical nature, which makes it possible to use a single and same tool to carry out on one hand the anchoring of fixing element 3 into support 2 and on the other hand the tightening of check screw 9.

Check screw 9 thus makes it possible to countersink head 3A into ring 6.

Moreover, device 1 is arranged such that the tightening of check screw 9 into countersink 8 causes axial expansion of ring 6, in a manner that brings the latter to expanded configuration.

Thus, in this preferred embodiment of the invention, axial expansion of ring 6 is obtained by tightening a check screw 9.

It is however completely possible to consider, without leaving the framework of the invention, to implement, means other than check screw 9 to realize the axial expansion of ring 6. It can therefore be considered that ring 6 includes an expandable portion, which can for example be inflated by a fluid of a liquid or gas type, the inflating of the expandable portion of the ring causing axial expansion of said ring. It can also be considered, in another example of realization, that ring 6 includes an elastic structure, of a spring type, with pretension, such that when pretension ceases, the spring slackens which leads to the axial expansion of ring 6. Ring 6 can thus notably be comprised of two rigid parts connected together by a compression spring, with the two parts being thrust one against the other so as to pretension the spring, and being interlocked in this thrust position. When interlocking is deactivated, the spring slackens, which leads to the separation of the parts and so to overall expansion, in the axial direction, of ring 6. Those skilled in the art shall be able to implement any other method known in the art in order to realize axial expansion.

Favorably, ring 6 includes two items, i.e. first and second items 10, 11, the substantially axial expansion of the ring to its expanded configuration corresponding to a relative separation of said items 10, 11 according to substantially axial direction X-X'.

Said items 10, 11 are more preferably of annular shape, and are positioned coaxially one in relation to the other in order to form ring 6.

Axial expansion thus corresponds to a relative separation of the first and second items 10, 11 according to movement that corresponds substantially to a translation in axial direction X-X'. This relative separation modifies the shape of the general lateral contour of ring 6, which changes for example from a spherical band shape allowing rotation of ring 6 in through hole 5, to a non-spherical band shape whose profile is composed of a first curved portion 10A attached to the first item, of a second curved portion 11A attached to a second item said curved portions 10A, 11A being separated by a primarily empty space.

This non-spherical band shape, because it is no longer complementary with the shape of internal wall 5A of hole 5, prevents all movement of ring 6 in hole 5.

Favorably, said two items 10, 11 are distinct and connected together by at least one bracket 12 having a flexible character in bending.

Thus, first and second items 10, 11 have more preferably a substantially rigid character, the capacity of axial deformation of ring 6 resulting mostly, even totally, from the deformable nature in the direction X-X' of a lug forming bracket 12.

For reasons of symmetry, it is privileged, in this embodiment, the implementation of two retaining brackets 12 diametrically opposed, said retaining brackets 12 linking said items 10, 11 together by their periphery.

By way of example, said retaining brackets 12 can for example be comprised of elastic lugs (for example made from plastic matter) or metallic blades folded in a V shape, such that the flexible character of brackets 12 corresponds to an unfolding of said brackets 12.

In an alternative embodiment of the invention, it is however completely possible to consider that first item 10 and second item 11 be totally independent one from the other, i.e. that they not be mechanically linked by a joining element such as bracket 12.

Favorably, countersink with internal threading 8 is distributed over the two items 10, 11 such that bore with internal thread 8A belongs, more preferably exclusively, to first item 10, while root 8B belongs, more preferably exclusively, to second item 11.

In this way, when check screw 9 is tightened, the latter comes to press against head 3A of fixing element 3 which rests as support against root 8B. The tightening effort of check screw 9 is thus going to produce a compression force against head 3A, said force generating, due to the independence of items 10, 11 bearing respectively bore with internal thread 8A and root 8B, a relative separation of said items 10, 11.

Favorably, when fixing element 3 is a screw, countersink 8 is threaded internally according to the opposite direction as that of the external threading 3C of said screw.

Favorably, first item 10 and through hole 5 are shaped in order to realize a spherical kinematic joint catch between said first item 10 and assembly part 4 when ring 6 is in its initial configuration. Said spherical joint catch substantially prohibits the rotation of first item 10 in an axial direction X-X' that is attached to it.

The realization of this joint allows to prevent the rotation on itself of first item 10 when check screw 9 is tightened into countersink 8 of said first item 10.

Favorably, the aforementioned spherical joint catch is realized by outfixing element first item 10 with at least one radial fin 6C, 6D destined to cooperate with a corresponding groove 7C, 7D of complementary shape arranged longitudinally on lateral wall 5A of through hole 5, such as to substantially prohibit the rotation of first item 10 around its axial direction X-X'.

A return in the torque of check screw 9 is thus obtained by the device 1 itself, without requiring the intervention of the user, or the use of a specific tool. Radial fins 6C, 6D are more preferably in the number of two, positioned on the lateral surface of first item 10 and projecting radially relative to axis X-X' of said first item 10.

Favorably, transversal section 13 of through hole 5 at the level of the upper side 4A and/or lower side 4B is shaped to allow the introduction into through hole 5 of ring 6 in initial configuration, and this only when said ring 6 is introduced via its edge 6B, as a coin is inserted into a moneybox.

To this end, the transversal section 13 of said through hole 5 at the level of the upper side 4A and/or lower side 4B, has more preferably a substantially circular general shape, with two additional undercuts 14, 15 diametrically opposed.

Said additional undercuts 14, 15 can be completed by grooves 7C, 7D, when ring 6 is equipped with radial fins 6C, 6D.

Thus, due to the fact that diameter D of the circular portion of transversal section 13 is less than the overall diameter d of ring 6, the latter cannot be completely inserted within through hole 5 unless it is introduced vertically, i.e. by its lateral flank 6B, in the zone extending between undercuts 14, 15.

In this way, once ring 6 is completely inserted into through hole 5, said ring 6 cannot be in a position to escape outside of said hole 5 unless it is placed in a position identical to that of its introduction position.

And, such an introduction position can no longer be reached once fixing element 3 is inserted into ring 6.

The arrangement described previously also makes it possible to passively maintain ring 6 captive in through hole 5, whether this ring is comprised of one or several items, and whether or not they are independent.

The configuration described previously, which furthermore corresponds to that shown in the figures, is however given only by way of example.

In place of a transversal section 13 of a generally circular shape, it is therefore completely possible to consider to allow for a transversal section 13 of a rectangular or square shape, or even polygonal shape.

The general principle of the invention relies on the fact that end sections 13 corresponding to the upper side 4A and lower side 4B of assembly part 4 have a shape that prohibits passage of ring 6 other than according to a predetermined orientation, here on edge 6B.

The invention also relates, independently, to a surgical implant 4 destined to be coupled to bone support 2, said implant having the aforementioned arrangement.

The invention also relates independently to a ring 6 destined to receive an osteosynthesis screw 3, said ring 6 including a first and second items 10, 11 substantially rigid, said items 10, 11 being superimposed and connected by a flexible part 12.

The realization and operation of the invention are now going to be described based on the example of a surgical device.

Figure 5:
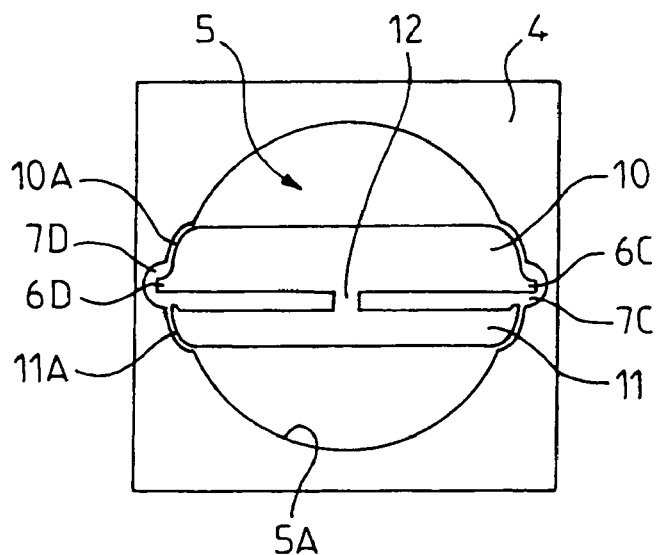
FIG. 5 shows, according to an overhead view, a manufacturing step of the device in accordance with the invention, wherein the ring shown in FIG. 4 is inserted into an assembly part shown in FIG. 3.

A ring 6 in accordance with the invention is introduced via its edge 6B into through hole 5 of an osteosynthesis plate 4, such as shown in FIG. 5.

Once ring 6 is completely introduced into through hole 5, said ring 6 is then pivoted around the passing axis by its axial fins 6C, 6D to be placed in a position to receive an osteosynthesis screw 3. Thus, a spherical joint catch is realized by the introduction into housing 5 of a single part, here ring 6, which is introduced without bending into through hole 5, which limits the risk of expulsion of ring 6 in service. At this stage, countersink with internal threading 8 of ring 6 and through hole 5 are substantially coaxial, or at least near to such coaxiality. Osteosynthesis screw 3 is then inserted into through hole 5 as well as into the countersink with internal threading 8 until it comes to a stop via its head 3A against root 8B of said countersink with internal threading 8.

According to the example shown in the figures, the axis of screw 3 and the axis X-X' of ring 6 are then substantially joined. It is however possible to consider, without leaving the framework of the invention, that such is not the case, which could occur if one considers that the axis of the countersink with external threading 8 differs from that of ring 6.

The practitioner then introduces a tightening tool into recess 3D of the screw and can tighten the latter into bone support 2 by selecting the angle between said screw 3 and plate 4, since screw 3 and ring 6 form a subset that is angularly moveable relative to plate 4.

Once anchoring of screw 3 is carried out within bone 2, the surgeon then proceeds with locking in angular position of plate 4 relative to screw 3, as well as with the sealing of the head of screw 3A, via tightening into countersink with internal threading 8 of a check screw 9. Check screw 9 will come to rest on the top of head 3A then progressively separate first item 10 from second item 11 forming ring 6. Check screw 9 therefore has a double function, i.e. on one hand a blocking function of the head of screw 3A, since the latter shall be held in compression between root 8B and check screw 9, and on the other hand an axial expansion function of ring 6, since once check screw 9 comes up against the head of screw 3A, any additional tightening provokes by reaction the separation of items 10, 11 comprising ring 6. Tightening check screw 9 takes place using a common standard tool, and does not require ring 6 to be maintained, since the latter is blocked in axial rotation by fins 6C, 6D. The tightening gestures of screw 3 and check screw 9 are therefore disassociated.

The device in accordance with the invention thus makes it possible to benefit from a particular stable and resistant mounting notably to the forces of pulling, shearing or sinking.

The device in accordance with the invention shows to be particularly effective in the case where the material of support 2 has a degree of hardness that is less than that of assembly part 4.

Finally, the proposed arrangement can be taken apart entirely.

The invention also relates to a method of therapeutic treatment implementing a device in accordance with the invention, and including notably the steps of mounting the ring in the through hole, of mounting a osteosynthesis screw in the ring, of tightening the screw in the bone, and axial expansion of the ring to block it in position in the through hole.

The invention claimed is:

1. A device (1) destined to be coupled to at least one support (2), said device (1) comprising:
   a fixing element including a head and a pin destined to be inserted in an axial direction in the support;
   an assembly part including at least one through hole; and
   a ring having a longitudinal axis corresponding to said axial direction and housed in a manner that can be oriented within said through hole, said ring being equipped with a passage extending substantially in said axial direction and being shaped on the one hand to allow passage of pin therethrough and on the other hand to realize a means of stoppage for head;
   wherein the ring is expandable according to substantially said axial direction between an initial configuration wherein ring can be oriented relative to hole and an expanded configuration wherein ring is blocked relative to hole.

2. The device (1) according to claim 1 wherein the through hole (5) and ring (6) are shaped to realize a spherical kinematic joint between assembly part (4) and ring (6) when ring (6) is in the initial configuration.

3. The device (1) according to claim 1 wherein the through hole (5) and ring (6) are shaped to realize a spherical kinematic joint catch between ring (6) and assembly part (4) when ring (6) is in the initial configuration, said spherical joint catch substantially prohibiting the rotation of ring (6) around its axial direction (X-X').

4. The device (1) according to claim 3 wherein the ring (6) includes at least one radial fin (6C, 6D) destined to cooperate with a corresponding groove (7C, 7D) of complementary shape arranged longitudinally on the lateral wall (5A) of through hole (5), such as to substantially prohibit the rotation of ring (6) around its axial direction (X-X').

5. The device (1) according to claim 1 wherein the passage (6A) includes a countersink with internal threading (8) defining a bore with internal threading (8A) and a root (8B), which root (8B) forms a support surface and a means of stoppage for said head (3A), said device including a check screw (9) destined to be tightened into countersink (8) against said head (3A), this tightening causing axial expansion of ring (6).

6. The device (1) according to claim 5 wherein the ring (6) includes a first item and a second item (10, 11) superimposed, and wherein the substantially axial expansion of ring (6) towards its expanded configuration corresponds to a relative separation of said first and second items (10, 11) according substantially to the axial direction (X-X').

7. The device according to claim 6 wherein said first and second items (10, 11) are distinct and connected together by at least one bracket (12) that has a flexible nature.

8. The device (1) according to claim 6 wherein said first and second items (10, 11) are independent one from the other.

9. The device (1) according to claim 6 wherein the countersink with internal threading (8) is distributed over the first and second items (10, 11) such that the bore with internal threading (8A) belongs to the first item (10) while root (8B) belongs to the second item (11).

10. The device (1) according to claim 6 wherein said first item (10) and through hole (5) are shaped to realize a spherical kinematic joint catch between the first item (10) and the assembly part (4) when ring (6) is in the initial configuration, said spherical joint prohibiting substantially the rotation of the first item (10) around its axial direction (X-X').

11. The device (1) according to claim 10 wherein the first item (10) includes at least one radial fin (6C, 6D) destined to cooperate with a corresponding groove (7C, 7D) of complementary shape arranged longitudinally on the lateral wall (5A) of through hole (5), such as to substantially prohibit the rotation of the first item (10) around its axial direction (X-X').

12. The device (1) according to claim 5 wherein the fixing element (3) is a screw.

13. The device (1) according to claim 12 wherein the countersink (8) is threaded internally according to a direction that is inverse to that of the external threading (3C) of the screw (3).

14. The device (1) according to claim 1 wherein the through hole (5) is arranged between an upper side (4A) and an opposite lower side (4B) of the assembly part (4), transversal section (13) of said hole (5) at the level of the upper side (4A) and/or lower side (4B) being shaped to allow the introduction in through hole (5) of ring (6) in initial configuration only when said ring (6) is introduced via its edge (6B).

15. The device (1) according to claim 14 wherein the transversal section (13) of said hole (5) at the level of the upper side (4A) and/or lower side (4B) has a substantially circular general shape, with two additional undercuts (14, 15) diametrically opposed.

16. The device (1) according to claim 1 wherein the support (2) is of a bone nature, while assembly part (4) is an implant or surgical ancillary.

17. The device (1) according to claim 16 wherein the assembly part (4) is an osteosynthesis plate.

* * * * *